United States Patent [19]

Marks et al.

[11] Patent Number: 4,505,898
[45] Date of Patent: Mar. 19, 1985

[54] DERIVATIVES OF ACETYLSALICYLIC ACID AND SUBSTITUTED PHENYLACETIC ACIDS AND COMPOSITIONS CONTAINING THEM

[76] Inventors: Robert E. Marks, 2 Burwood Close, Merrow, Guildford, Surrey; James S. Burton, The Barn Cottage, Bunch La.; John A. Elvidge, Kylemore, Derby Rd., both of Haslemere, Surrey; Saresh Shah, 2 Chestnut Grove, Tottenham, London N17, all of England

[21] Appl. No.: 548,528

[22] Filed: Oct. 27, 1983

Related U.S. Application Data

[62] Division of Ser. No. 370,657, Apr. 21, 1982, Pat. No. 4,452,783.

[51] Int. Cl.³ .................... C07C 103/52; A61K 37/02
[52] U.S. Cl. .............................. 514/18; 260/112.5 R; 514/19
[58] Field of Search ................. 260/112.5 R; 424/177

[56] References Cited

U.S. PATENT DOCUMENTS

| | | | |
|---|---|---|---|
| 3,326,886 | 6/1967 | Kominato | 424/177 |
| 3,927,082 | 12/1975 | Katori et al. | 562/444 |
| 4,123,544 | 10/1978 | Kornowski et al. | 548/533 |
| 4,452,783 | 1/1984 | Marks et al. | 424/177 |

FOREIGN PATENT DOCUMENTS 2083457 3/1982 United Kingdom .

*Primary Examiner*—Delbert R. Phillips
*Assistant Examiner*—F. T. Moezie

[57] ABSTRACT

Peptide derivatives of the formula

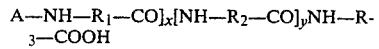

$$A-NH-R_1-CO]_x[NH-R_2-CO]_yNH-R_3-COOH$$

in which A, $R_1$, $R_2$, $R_3$, x, and y have the meaning specified in claim 1 and their physiologically acceptable salts and lower alkyl esters.

These compounds have anti-inflammatory activity and pharmaceutical compositions containing them are described.

9 Claims, No Drawings

DERIVATIVES OF ACETYLSALICYLIC ACID AND SUBSTITUTED PHENYLACETIC ACIDS AND COMPOSITIONS CONTAINING THEM

This application is a division of our prior copending application Ser. No. 370,657, filed Apr. 21, 1982, now U.S. Pat. No. 4,452,783.

This invention is concerned with derivatives of acetylsalicylic acid and 4-allyloxy-3-chlorophenylacetic acid and its saturated analogue, 4-n-propoxy-3-chlorophenylacetic acid and with pharmaceutical compositions containing such derivatives.

Acetylsalicylic acid, Aspirin, and 4-allyloxy-3-chloro-phenylacetic acid, Alclofenac, are well known anti-inflammatory agents and have been widely used for many years for this purpose. Both compounds, however, have undesirable side effects or properties which have contra-indicated their use for extended periods of treatment and/or for particular patients. Thus Aspirin causes gastric irritation and, in some cases, ulcerative lesions in the stomach. Alclofenac causes skin rashes in some patients and it has further been reported that when metabolised the terminal olefinic group of Alclofenac is converted into an epoxide which has mutagenic properties. Such an epoxide cannot be formed from the saturated analogue of Alclofenac, 4-n-propoxy-3-chlorophenylacetic acid, but this compound has much reduced anti-inflammatory activity as compared with Alclofenac.

Despite these disadvantages, the need for non-steroidal anti-inflammatory drugs has lead to the continued use of Aspirin and Alclofenac for this purpose.

We have now found that the anti-inflammatory activity of these well known compounds is largely or wholly retained and their undesirable side effects are reduced or eliminated in certain aminoacid and peptide derivatives thereof. We have further surprisingly found that aminoacid and peptide derivatives of the saturated analogue of Alclofenac have substantially as good anti-inflammatory activity as Alclofenac and such derivatives are incapable of giving rise to a mutagenic epoxide on being metabolised just as the saturated analogue itself.

According to the present invention, therefore, we provide a pharmaceutical composition comprising at least one aminoacid or peptide derivative of the formula:

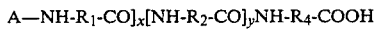

in which A is acetylsalicyloyl, 4-allyloxy-3-chloro-phenylacetyl or 4-n-propoxy-3-chloro-phenylacetyl, $R_1$, $R_2$ and $R_3$, which may be the same or different, are a residue of an α-aminoacid, x is 0 or 1, y is 1 when A is acetylsalicyloyl and is 0 or 1 when A is 4-allyloxy-3-chloro-phenylacetyl or 4-n-propoxy-3-chloro-phenylacetyl, or a physiologically acceptable salt or lower alkyl ester thereof, and an inert, physiologically acceptable carrier or excipient.

Suitable α-aminoacids, $H_2N$-$R_1$-COOH, $H_2N$-$R_2$-COOH and $H_2N$-$R_3$-COOH, for forming the derivatives of formula I are, for example, glycine, alanine, valine, leucine, isoleucine, serine, homoserine, threonine, proline, hydroxyproline, cysteine, homocysteine, methionine, phenylalanine, tyrosine, dopa, tryptophan, ornithine, lysine, hydroxylysine, histidine, aspartic acid, asparagine, glutamic acid and glutamine. Of these, glycine, alanine, histidine and phenylalanine are preferred.

Since the majority of α-aminoacids exist in stereoisomeric forms, it will be appreciated that many of the compounds of formula I will have two or more such forms and the individual stereoisomeric forms of the compounds or their racemic mixtures can be used in the compositions according to the invention.

Preferred compounds of formula I for use according to the invention are those in which:
A is 4-allyloxy-3-chloro-phenylacetyl or 4-n-propoxy-3-chloro-phenylacetyl,
x is 0,
y is 0 or 1, and
$R_2$ and $R_3$ are residues derived from glycine, alanine, or phenylalanine.

Of these, particularly preferred compounds are:
4-allyloxy-3-chloro-phenylacetyl-alanine methyl ester,
4-allyloxy-3-chloro-phenylacetyl-glycine, and
4-n-propoxy-3-chloro-phenylacetyl-glycine.

The pharmaceutical compositions according to the invention may be formulated for oral or parenteral administration and suitable carriers therefor will be well known to those skilled in the art. Orally administrable compositions in the form of tablets or capsules are generally preferred.

All the compounds of formula I are novel with the exception of 4-allyloxy-3-chloro-phenylacetylglycine (I, A=Alclofenac residue; x=y=0, $R_3$=$CH_2$) which has been positively identified as a metabolite of Alclofenac in hydrolysed pig urine and which has been synthesized (see R. Roncucci et al, Mass Spectrometry in Biochemistry and Medicine, ed. A. Frigerio and N. Castagnoli, Raven Press, New York, 1974, p.29–56, particularly pp.48–49).

The present invention also comprises, therefore, aminoacid and peptide derivatives of the formula:

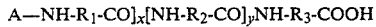

in which A, $R_1$, $R_2$, x and y have the meanings stated above for formula I and $R_4$ is a residue of an α-aminoacid which, when A is 4-allyloxy-3-chloro-phenylacetyl and x and y are 0, contains at least 2 carbon atoms, and their physiologically acceptable salts and lower alkyl esters.

Suitable exemplary α-aminoacids and preferred aminoacids for forming the compounds according to the invention are as stated above in relation to the compositions according to the invention. Again as stated above, the present invention includes both the individual stereoisomeric forms of the compounds (where such exist) and their racemic mixtures.

Preferred compounds of formula II are those in which:
(a)
A is 4-allyloxy-3-chloro-phenylacetyl,
x and y are 0, and
$R_4$ is a residue derived from alanine or phenylalanine.
(b)
A is 4-n-propoxy-3-chloro-phenylacetyl,
x is 0,
y is 0 or 1, and
$R_2$ and $R_4$ are residues derived from glycine, alanine or phenylalanine.

Of these, particularly preferred new compounds according to the invention are:

4-allyloxy-3-chloro-phenylacetyl-alanine methyl ester, and 4-n-propoxy-3-chloro-phenylacetyl-glycine.

The compounds according to the invention can be prepared by the conventional procedures of peptide chemistry from known compounds. The starting compounds are one of the acids, acetylsalicylic acid, 4-allyloxy-3-chloro-phenylacetic acid or 4-n-propoxy-3-chlorophenylacetic acid, and the aminoacid or aminoacids, the residue or residues of which are required in the desired product. Where the desired compound contains two or three aminoacid residues, that is x and/or y in the above formulae is 1, a di- or tri-peptide can first be formed from the aminoacids and the di- or tri-peptide then coupled with one of the acids mentioned above, but we have found it preferable to make such compounds by building up the peptide chain progressively on the acid, that is by coupling the first aminoacid to the acid to form a first intermediate, then coupling the second aminoacid to the first intermediate and, where a tri-peptide chain is required, coupling the third aminoacid to the end of the di-peptide chain. In referring to first, second and third aminoacids, it is to be understood that they need not be different and the same aminoacid may be used in more than one stage.

As is well known, the formation of peptide linkages normally proceeds by way of the following stages:
 (i) protection of any reactive groups present in the starting compounds which are not required to react to obtain the desired peptide bond,
 (ii) conversion of either the carboxyl group of one starting compound or the amino group of the other starting compound into a reactive derivative thereof, the "activation" stage,
 (iii) interaction of the activated starting compound with the other protected starting compound to form the desired peptide bond, and
 (iv) removal of the protecting groups from the product of step (iii).

In the case of the compounds according to the invention, it is convenient to proceed by way of carboxyl group activation in step (ii). In the case of neutral aminoacids, that is those containing one amino group and one carboxyl group, no protection is required for the amino group since it is the latter which reacts with the activated carboxyl group of the other reactant. Carboxyl groups are preferably protected by forming a salt, preferably an alkali metal salt, or an ester, preferably a lower alkyl ester, the latter procedure generally being preferred.

Many methods of carboxyl group activation are known in peptide chemistry; any of them can, in principle, be used in preparing the compounds according to the invention. Suitable methods include, for example, the following:

(1) Mixed anhydride method

This method involves the formation of a mixed anhydride by reaction between the carboxyl group of the starting compound and an alkyl chloroformate, for example ethyl chloroformate:

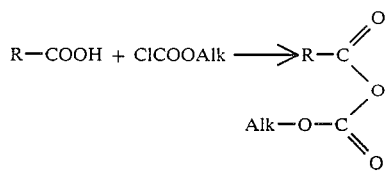

The mixed anhydrides are formed at a low temperature in an organic solvent, such as tetrahydrofuran. The reaction with the free amino group starting material is also carried out at low temperatures, for example 0° C. or below, and gives good yields, carbon dioxide and an alcohol, Alk-OH, being the other products in addition to the desired peptide.

(2) N,N'-Dicyclohexylcarbodiimide method

This method involves the reaction of the free acid starting material with N,N'-dicyclohexylcarbodiimide to obtain an activated compound which is believed to be an O-acylisourea of the formula:

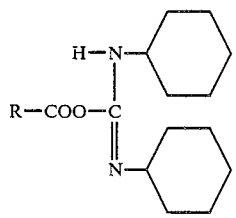

(3) Azide method

The activated starting material has the formula:

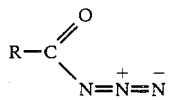

and is formed by esterifying the free acid starting material to form a lower alkyl, preferably methyl or ethyl, ester thereof, reacting the latter with hydrazine to form an acid hydrazide, and reacting the latter with nitrous acid to form the azide.

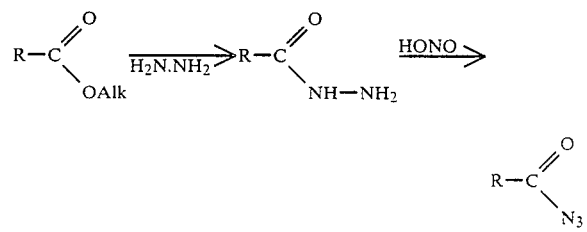

(4) Activated ester method

A number of esters which are very much more reactive with amino groups than simple alkyl esters, have been described. A generally preferred ester is the p-nitrophenyl ester; this reacts with amino groups a thousand times faster than the corresponding methyl ester.

(5) N,N'-Carbonyldiimidazole method

The activated starting material is an acylimidazole of the formula:

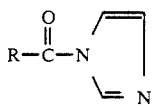

formed by reaction between the free acid starting material and carbonyldiimidazole in an organic solvent, such as tetrahydrofuran.

Suitable reaction conditions for the four stages of protection, activation, interaction and removal of protective groups will be known to those skilled in the art or readily ascertainable by routine experimentation. Isolation of intermediate products is usually not required, but where desirable can be carried out by conventional procedures, as can be the isolation and purification of the desired final product.

Compounds of formulae I and II in which A is 4-n-propoxy-3-chloro-phenylacetyl can be obtained either by using the corresponding acid, 4-n-propoxy-3-chloro-phenylacetic acid, as a starting material or by using 4-allyloxy-3-chloro-phenylacetic acid as a starting material and hydrogenating the or an intermediate product or the final product to reduce the allyloxy substituent to n-propoxy. Such hydrogenation can be carried out by any of the conventional processes therefor and suitable reaction conditions will be known to those skilled in the art.

In order that the invention may be more fully understood, the following examples are given by way of illustration.

EXAMPLE 1

Acetylsalicyloyl-(DL)-alanyl-(DL)-alanine
(i) Acetylsalicyloyl-(DL)-alanine:

Acetylsalicylic acid (18.0 g) was dissolved in dry tetrahydrofuran (50 ml) and dry triethylamine (13.8 ml) was added to the solution and the whole was cooled to −5° C. in a dry ice-acetone bath. After stirring the mixture for 5 min., redistilled ethyl chloroformate (9.6 ml) was added dropwise over a period of 20 min. The mixture was stirred for a further 5 min. and then aminolysis was carried out by adding a solution of (DL)-alanine (8.9 g) in aqueous sodium hydroxide (1M, 100 ml) and stirring was continued at 0° C. for 6 hrs.

Volatile material was removed at reduced pressure and 30° C. and the residual solution was acidified with dilute hydrochloric acid, (3M), to pH 2–3, and quickly extracted with ethyl acetate (100 ml). After drying the ethyl acetate extract (over anhydrous sodium sulphate), the solvent was evaporated at reduced pressure. The oily residue was treated with light petroleum (b.p. 40°–60° C.) with cooling until crystals began to form. A solid (10.0 g) m.p. 80°–90° C., was obtained and after six recrystallisations from chloroform/light petroleum (b.p. 40°–60° C.), it gave acetylsalicyloyl-(DL)-alanine (5.0 g) m.p. 118°–120° C.

Analysis: found C,57.33; H,5.16; N,5.35. $C_{12}H_{13}O_5N$ requires C,57.36; H,5.21, N,5.57%

(ii) Acetylsalicyloyl-(DL)-alanyl-(DL)-alanine:

Acetylsalicyloyl-(DL)-alanine (2.5 g) was dissolved in dry tetrahydrofuran (15.0 ml) and dry triethylamine (1.36 ml) was added. The reaction mixture was brought to −5° C. and ethyl chloroformate (0.96 ml) was added dropwise over a period of 10 min. (DL)-Alanine (0.89 g) dissolved in aqueous sodium hydroxide (1M, 10.0 ml) was added. The reaction was allowed to proceed at 0° C. for 6 hrs., and the solvent was then removed at 30° C.

under reduced pressure. The residual solution was acidified to pH 2–3 using aqueous hydrochloric acid (3M). The whole was extracted with ethyl acetate (50.0 ml), and the extract was dried (anhydrous sodium sulphate). The bulk of the ethyl acetate was removed under reduced pressure to leave a small volume of solution.

The complete removal of the solvent, ethyl acetate, left an oily material (1.5 g); on adding light petroleum (b.p. 40°–60° C.); a gummy material (1.15 g) consisting mainly of the desired product was recovered. The material was not crystallisable.

EXAMPLE 2

4-Allyloxy-3-chloro-phenylacetyl-(DL)-alanine methyl ester

A suspension of (DL)-alanine methyl ester hydrochloride (2.8 g) in dry methylene chloride (10 ml) containing dry triethylamine (2.8 ml) was added to a solution of 4-allyloxy-3-chloro-phenylacetic acid (4.3 g) in dry methylene chloride (30 ml). N,N'-dicyclohexyl-carbodiimide (DCC; 4.1 g) was added and the reaction mixture was stirred at room temperature.

After overnight stirring, the reaction mixture was cooled 0° C. and the by-product, N',N-dicyclohexylurea (DCU) was filtered off. The volatile material was removed by evaporation under reduced pressure. The semi-solid residue was dissolved in chloroform (50 ml). The chloroform solution was washed with aqueous hydrochloric acid (0.5M, 2×20 ml), saturated aqueous sodium bicarbonate solution (2×20 ml) and finally with water (2×20 ml).

The extract was dried (anhydrous sodium sulphate) and then evaporated to a small volume under reduced pressure. Light petroleum (50 ml, b.p. 60°–80° C.) was added to obtain a solid product (2.0 g) m.p. 58°–63° C. After recrystallisation from chloroform/light petroleum (b.p. 60°–80° C.) the abovenamed product, (1.4 g), m.p. 60°–63° C., was obtained.

Found: C,57.54; H,5.80; N,4.41; Cl,11.40. $C_{15}H_{18}NO_4Cl$ requires C,57.79; H,5.82; N,4.49; Cl,11.37%

EXAMPLE 3

4-Allyloxy-3-chloro-phenylacetyl-(DL)-alanine
4-Allyloxy-3-chloro-phenylacetyl-(DL)-alanine methyl ester (2.0 g) was suspended in acetone (20 ml). Aqueous sodium hydroxide (1M, 8.0 ml) was added and the mixture was gently warmed to effect solution, and then heated at 40° C. for 20 min. After the solution has been cooled, the pH was adjusted to 2–3 using dilute hydrochloric acid (3M) and the product was extracted with ethyl acetate (40 ml). The extract was dried (anhydrous sodium sulphate). The solvent was evaporated at reduced pressure to leave a solid residue (1.8 g); it had m.p. 120°–124° C. After recrystallisation from ethyl acetate/light petroleum (b.p. 60°–80° C.) the above-named product, (1.6 g), m.p. 123°–124° C. was obtained.

Found: C,56.54; H,5.46; N,4.74; Cl,11.74. $C_{14}H_{16}NO_4Cl$ requires C,56.47; H,5.42; N,4.71; Cl,11.90%

EXAMPLE 4

4-Allyloxy-3-chloro-phenylacetyl-(DL)-alanyl-(DL)-alanine methyl ester

4-Allyloxy-3-chloro-phenylacetyl-(DL)-alanine (0.622 g) was dissolved in dry tetrahydrofuran (10 ml). To the solution was added (DL)-alanine methyl ester hydrochloride (0.3 g) in dry methylene chloride (3.0 ml) containing dry triethylamine (0.3 ml). DCC (0.413 g) was added and the reaction mixture was stirred at room temperature. After being stirred overnight, the reaction mixture was worked up. DCU was filtered off. The volatile material was evaporated at reduced pressure. The semi-solid residue was dissolved in chloroform (20 ml). The chloroform solution was washed with aqueous hydrochloric acid (0.5M, 2×20 ml), saturated aqueous sodium bicarbonate solution (2×20 ml) and finally with water (2×20 ml). The extract was dried (anhydrous sodium sulphate). The solvent was evaporated at reduced pressure to leave a small volume of material. Light petroleum (b.p. 60°–80° C.) was added to obtain a solid product (400 mg) of m.p. 100°–105° C. After recrystallisation from chloroform/light petroleum (b.p. 60°–80° C.) the above-named product, (200 mg), m.p. 105°–107° C., was obtained.

Found: C,56.44; H,5.99; N,7.22; Cl,8.99. $C_{18}H_{23}N_2O_5Cl$ requires: C,56.46; H,6.05; N,7.32; Cl,9.26%

EXAMPLE 5

4-Allyloxy-3-chloro-phenylacetyl-glycine ethyl ester

4-Allyloxy-3-chloro-phenylacetic acid (4.3 g) was dissolved in dry tetrahydrofuran (20 ml). To the solution was added glycine ethyl ester hydrochloride (2.85 g) in dry chloroform (30 ml) containing dry triethylamine (2.8 ml). DCC (4.1 g) was added and the reaction mixture was stirred overnight at room temperature.

DCU was filtered off and the volatile material was evaporated at reduced pressure. The semi-solid residue was dissolved in chloroform (100 ml). The chloroform solution was washed with dilute hydrochloric acid (0.5M, 2×50 ml), saturated aqueous sodium bicarbonate (2×50 ml) and finally with water (2×50 ml). The extract was dried (anhydrous sodium sulphate).

The solvent was evaporated at reduced pressure to leave a small volume of material. Light petroleum (b.p. 60°–80° C.) was added to obtain a solid (2.0 g) of m.p. 70°–73° C. After recrystallisation from chloroform/light petroleum (b.p. 60°–80° C.), the above-named product, (1.4 g), m.p. 73°–76° C. was obtained.

Found: C,57.94; H,5.77; N,4.78; Cl,11.17. $C_{15}H_{18}NO_4Cl$ requires C,57.79; H,5.82; N,4.49; Cl,11.37%

EXAMPLE 6

4-Allyloxy-3-chloro-phenylacetyl-glycine methyl ester

The procedure of Example 5 was repeated, but using glycine methyl ester hydrochloride (2.3 g) in dry chloroform (20 ml) containing dry triethylamine (2.8 ml).

Following addition of light petroleum (b.p. 60°–80° C.) to the evaporated dried extract, 2.0 g of a solid, m.p. 68°–73° C., were obtained. After recrystallisation from chloroform/light petroleum (b.p. 60°–80° C.), the above-named product (1.5 g), m.p. 70°–73° C., was obtained.

Found: C,56.44; H,5.73; N,4.93; Cl,11.74; $C_{14}H_{16}NO_4Cl$ requires C,56.47; H,5.42; N,4.71; Cl, 11.90%

EXAMPLE 7

4-Allyloxy-3-chloro-phenylacetyl-glycine

4-Allyloxy-3-chloro-phenylacetyl-glycine methyl ester (0.594 g) was suspended in acetone (8.0 ml) to which was added aqueous sodium hydroxide solution (1M, 4.0 ml) and the whole was warmed to 40° C. for 30 min. After the solution had been cooled to 0° C., the pH was adjusted to 2–3 using dilute hydrochloric acid (3M) and quickly extracted with ethyl acetate (20 ml). The extract was dried (anhydrous sodium sulphate). The solvent was evaporated at reduced pressure to leave a solid residue (450 mg), m.p. 115°–119° C. After recrystallisation from ethyl acetate/light petroleum (b.p. 60°–80° C.) the above-named product, m.p. 117°–119° C., was obtained.

Found: C,54.86; H,4.70; N,4.94; Cl,12.72. $C_{13}H_{14}NO_4Cl$ requires C,55.03; H,4.97; N,4.94; Cl,12.50%

EXAMPLE 8

4-Allyloxy-3-chloro-phenylacetyl-(L)-histidine methyl ester

4-Allyloxy-3-chloro-phenylacetic acid (4.3 g) was dissolved in dry tetrahydrofuran (40 ml). To the solution was added (L)-histidine methyl ester dihydrochloride (4.8 g) in dry chloroform (20 ml) containing dry triethylamine (5.6 ml). DCC (4.1 g) was added and the reaction mixture was stirred overnight at room temperature.

DCU was filtered off and the volatile material was evaporated at reduced pressure. The semi-solid residue was dissolved in ethyl acetate (50 ml). The ethyl acetate solution was washed with dilute hydrochloric acid (pH 4.6, 2×100 ml), saturated aqueous sodium bicarbonate solution (2×100 ml), and finally with water (2×100 ml). The extract was dried (anhydrous sodium sulphate). The solvent was evaporated at reduced pressure to leave a solid residue (3.0 g), m.p. 89°–93° C. After recrystallisation from ethyl acetate/light petroleum (b.p. 60°–80° C.) the above-named product (2.2 g), m.p. 90°–93° C., was obtained.

Found: C,57.57; H,5.59; N,10.88; Cl,9.05. $C_{18}H_{20}N_3O_4Cl$ requires C,57.22; H,5.34; N,11.12; Cl,9.38%

$[\alpha]_D^{20°} = -11.58°$

EXAMPLE 9

4-Allyloxy-3-chloro-phenylacetyl-glycyl-(L)-histidine methyl ester

4-Allyloxy-3-chloro-phenylacetyl-glycine (4.3 g) was dissolved in dry tetrahydrofuran (40 ml). To the solution was added (L)-histidine methyl ester dihydrochloride (4.84 g) in dry chloroform (20 ml) containing dry triethylamine (5.60 ml). DCC (4.1 g) was added and the reaction was stirred overnight at room temperature.

DCU was filtered off and the volatile material was evaporated at reduced pressure. The semi-solid residue was dissolved in ethyl acetate (100 ml). The ethyl acetate solution was washed with aqueous hydrochloric acid (pH 4.6, 2×100 ml), saturated aqueous sodium bicarbonate solution (2×100 ml), and finally with water. The extract was dried (anhydrous sodium sulphate). The solvent was evaporated at reduced pressure to leave a solid residue (1.1 g), m.p. 145°–149° C.

The solid product was treated with hot chloroform (30 ml) and the insoluble material was filtered off. Light petroleum (b.p. 40°–60° C.) was added (50 ml) and a solid (0.7 g), m.p. 147°–150° C., was obtained. This product was recrystallised from acetone/light petroleum (b.p. 60°–80° C.) to give the above-named product (520 mg), m.p. 153°–155° C.

Found: C,55.21; H,5.36; N,12.61; Cl,8.18. C$_{20}$H$_{23}$N$_4$O$_5$Cl requires C,55.23; H,5.33; N,12.89; Cl,8.15%

EXAMPLE 10

4-Allyloxy-3-chloro-phenylacetyl-(L)-histidineglycine ethyl ester (i) 4-Allyloxy-3-chloro-phenylacetyl-(L)-histidyl hydrazine:

4-Allyloxy-3-chloro-phenylacetyl-(L)-histidine methyl ester (300 mg) was dissolved in absolute ethanol (10 ml). Hydrazine hydrate (62%, 3.0 ml) was added to the solution. The mixture was left standing overnight at room temperature. The solid product was filtered off and then washed with dry ether and then dried. The product, 4-allyloxy-3-chlorophenylacetyl-(L)-histidyl hydrazide, had m.p. of 203°-206° C.

The compound could not be recrystallised as it was found to be insoluble in common organic solvents: chloroform, carbon tetrachloride, methanol, ethanol, dimethylformamide, acetone, tetrahydrofuran, cyclohexane, nitrobenzene, benzene, dioxan, dimethylsulphoxide, and diethyl ether. It was also found to be insoluble in water.

Found: C,53.97; H,5.43; N,18.42; Cl,9.60. C$_{17}$H$_{20}$N$_5$O$_3$Cl requires C,54.04; H,5.34; N,18.54; Cl,9.38%.

(ii) 4-Allyloxy-3-chloro-phenylacetyl-(L)-histidylglycine ethyl ester:

4-Allyloxy-3-chloro-phenylacetyl-(L)-histidine hydrazide (1.51 g) in dilute hydrochloric acid (1M, 12 ml) was suspended in ethyl acetate (16 ml) and the whole was cooled in an ice bath. A cold solution of sodium nitrite (280 mg) in distilled water (2 ml) was added. After 2 min., cold potassium carbonate (50% w/v, 2.4 ml) was added and the mixture was placed in a separating funnel. The aqueous solution was separated from the organic phase. The former was extracted with ethyl acetate (2 ml) and the combined organic extracts were dried (anhydrous sodium sulphate).

Aqueous potassium carbonate (50% w/v, 6.0 ml) was added to a suspension of glycine ethyl ester hydrochloride (0.558 g) in dry ether (16 ml) at 0° C. The mixture was placed in a separating funnel and the organic layer separated and then dried (anhydrous sodium sulphate). The two dried extracts were mixed and left to stand at 0° C. for 24 hr. The crude solid product which formed was filtered off, washed with a little ethyl acetate and dried. The product (500 mg) has an m.p. of 160°-170° C.

Three preparations on this scale were carried out and the product were bulked. After recrystallisation from acetone/light petroleum (b.p. 60°-80° C.), the above-named product (750 mg), m.p. 165°-167° C., was obtained.

Found: C,56.14; H,5.35; N,12.16; Cl,7.98. C$_{21}$H$_{25}$N$_4$O$_5$Cl requires C,56.18; H,5.61; N,12.48; Cl,7.90%.

EXAMPLE 11

4-Allyloxy-3-chloro-phenylacetyl-glycyl-glycine

4-Allyloxy-3-chloro-phenylacetyl-glycine (2.83 g) was dissolved in dry tetrahydrofuran (10 ml). To it was added N,N'-carbonyldiimidazole (CDI; 1.62 g) and the reaction mixture was stirred for 30 min. until effervescence ceased. Glycine (0.75 g) in aqueous sodium hydroxide (1M, 10.0 ml) was then added and the reaction mixture was stirred at room temperature for 1 hr.

The reaction mixture was then poured into dilute hydrochloric acid (pH 2-3, 50 ml) and the oily layer formed was extracted with ethyl acetate (100 ml) and the extract was dried (anhydrous sodium sulphate). The solvent was evaporated to leave a small volume of material. Light petroleum (b.p. 60°-80° C.) was added to precipitate the solid (1.2 g) of m.p. 165°-174° C.

After recrystallisation, to a constant melting point, from methanol the above-named product (700 mg), m.p. 170°-174° C., was obtained.

Found: C,52.67; H,5.00; N,8.20; Cl,10.51; C$_{15}$H$_{17}$N$_2$O$_5$Cl requires C,52.87; H,5.03; N,8.22; Cl,10.40%.

EXAMPLE 12

4-Allyloxy-3-chloro-phenylacetyl-glycine methyl ester (i) 4-Allyloxy-3-chloro-phenylacetic acid p-nitrophenyl ester 4-Allyloxy-3-chloro-phenylacetic acid (4.3 g) was dissolved in dry tetrahydrofuran (20 ml). To the solution was added p-nitrophenol (2.28 g) in dry chloroform (30 ml). DCC (4.1 g) was then added and the whole was then stirred at room temperature overnight.

DCU was filtered off. The volatile material was evaporated at reduced pressure. The solid residue was dissolved in chloroform (100 ml). The chloroform solution was washed with saturated aqueous sodium bicarbonate solution (2×50 ml) and then with water. The extract was dried (anhydrous sodium sulphate) and then decolorised with charcoal.

The solvent was evaporated at reduced pressure to leave a small volume of material. Light petroleum (b.p. 40°-60° C.) was added to give the solid (2.0 g) of m.p. 66°-67° C. After recrystallisation form diethyl ether, the p-nitrophenyl ester (1.5 g), m.p. 66°-69.5° C., was obtained.

Found: C,58.84; H,3.89; N,4.28; Cl,10.23. C$_{17}$H$_{14}$NO$_5$Cl requires C,58.71; H,4.06; N,4.03; Cl,10.19%.

(ii) 4-Allyloxy-3-chloro-phenylacetyl-glycine methyl ester:

4-Allyloxy-3-chloro-phenylacetic acid p-nitrophenyl ester (3.69 g) was dissolved in chloroform (30 ml). To the solution was added glycine methyl ester hydrochloride (1.5 g) in dry chloroform (30 ml) containing dry triethylamine (1.4 ml), and the solution was stirred at 40° C. for 4 hrs.

The reaction mixture was washed with saturated aqueous sodium bicarbonate solution (2×50 ml) and then with water (2×50 ml). It was dried (anhydrous sodium sulphate). After treating with charcoal, the solvent was evaporated at reduced pressure to leave a small volume of material. Light petroleum (b.p. 60°-80° C.) was added to give a solid (2.0 g) of m.p. 68°-73° C. After recrystallisation from chloroform/light petroleum (b.p. 60°-80° C.) the above-named product (1.8 g), m.p. 70°-73° C., was obtained.

EXAMPLE 13

4-Allyloxy-3-chloro-phenylacetyl-(L)-phenylalanine methyl ester

4-Allyloxy-3-chloro-phenylacetic acid p-nitrophenyl ester (3.69 g) was dissolved in chloroform (30 ml). To the solution, (L)-phenylalanine methyl ester hydrochloride (4.32 g) in dry chloroform (50 ml) containing dry triethylamine (2.8 ml) was added and the mixture was stirred at 40° C. for 4 hrs.

The reaction mixture was then washed with saturated aqueous sodium bicarbonate solution (2×50 ml), and then with water (2×50 ml). It was dried (anhydrous sodium sulphate). After treating with charcoal, the solvent was evaporated at reduced pressure to leave a small volume of material. Light petroleum (b.p. 80°–100° C.) was added; the solid (3.0 g) of m.p. 65°–70° C. was precipitated. After recrystallisation from chloroform/light petroleum (b.p. 80°–100° C.), the above-named product (2.4 g), m.p. 67°–70° C., was obtained.

Found: C,64.95; H,5.50; N,3.65; Cl,9.09. $C_{21}H_{22}NO_4Cl$ requires C,65.03; H,5.72; N,3.61; Cl,9.14%.

$[\alpha]_D^{20°} = -6.28°$

EXAMPLE 14

4-Allyloxy-3-chloro-phenylacetyl-(L)-phenylalanine

4-Allyloxy-3-chloro-phenylacetyl-(L)-phenylalanine methyl ester (3.5 g) was suspended in acetone (70 ml) to which was added aqueous sodium hydroxide (1M, 18 ml) and heated gently to effect solution. The reaction mixture was kept warm at 40° C. for 30 min.

After the solution had been cooled to 0° C., the pH was adjusted to 2–3 using dilute hydrochloric acid (3M), and then extracted with ethyl acetate (50 ml). The extract was dried (anhydrous sodium sulphate) and the volatile material was evaporated at reduced pressure to give a small volume of material, light petroleum (b.p. 80°–100° C.) was added to precipitate the solid (2.4 g) of m.p. 111°–116° C. After recrystallisation from ethyl acetate/light petroleum (b.p. 80°–100° C.) the above-named product (1.8 g), m.p. 114°–116° C., was obtained.

Found: C,64.01; H,5.30; N,3.69; Cl,9.53; $C_{20}H_{20}NO_4Cl$ requires C,64.26; H,5.39; N,3.75; Cl,9.48%.

EXAMPLE 15

4-Allyloxy-3-chloro-phenylacetyl-(L)-phenylalanyl-(L)-phenylalanine methyl ester 4-Allyloxy-3-chloro-phenylacetyl-(L)-phenylalanine (1.87 g) was dissolved in dry tetrahydrofuran (10 ml). To the solution was added (L)-phenylalanine methyl ester hydrochloride in dry chloroform (10 ml) containing dry triethylamine (0.7 ml). DCC (1.02 g) was added and the reaction mixture was stirred overnight.

DCU was filtered off. The volatile material was removed at reduced pressure. The semi-solid residue was dissolved in chloroform (50 ml). The chloroform solution was washed with dilute hydrochloric acid (0.5M, 2×20 ml), saturated aqueous sodium bicarbonate solution (2×20 ml), and finally with water (2×20 ml). The extract was dried (anhydrous sodium sulphate). The solvent was evaporated to leave a small volume of material. Light petroleum (b.p. 80°–100° C.) was added to give a solid (700 mg) of m.p. 114°–120° C. After recrystallisation from chloroform/light petroleum (b.p. 80°–100° C.), the above-named product (600 mg), m.p. 118°–120° C., was obtained.

Found: C,67.27; H,5.80; N,5.42; Cl,6.76; $C_{30}H_{31}N_2O_5Cl$ requires C,67.34; H,5.84; N,5.24; Cl,6.63%.

EXAMPLE 16

4-Allyloxy-3-chloro-phenylacetyl-(L)-phenylalanyl-(L)-phenylalanine

4-Allyloxy-3-chloro-phenylacetyl-(L)-phenylalanyl-(L)-phenylalanine methyl ester (5.3 g) was suspended in acetone (40 ml) to which was added aqueous sodium hydroxide (1M, 20.0 ml) and the whole was heated to effect solution. After the solution had been cooled to 0° C., the pH was adjusted to 2–3 using aqueous hydrochloric acid (3M) and the whole was extracted with ethyl acetate (80 ml). The extract was dried (anhydrous sodium sulphate) and the solvent was evaporated at reduced pressure to leave a small volume of material. Light petroleum (b.p. 80°–100° C.) was added to precipitate the solid (3.5 g) of m.p. 180°–186° C. After recrystallisation from ethyl acetate/light petroleum (b.p. 80°–100° C.), the above-named product (2.7 g), m.p. 183°–186° C., was obtained.

Found: C,66.99; H,5.47; N,5.32; Cl,6.85; $C_{29}H_{29}N_2O_5Cl$ requires C,66.85; H,5.61; N,5.38; Cl,6.80%.

EXAMPLES 17–20

Examples 13–16 were repeated but using (DL)-phenylalanine methyl ester hydrochloride instead of the (L)-isomer to give the following products:

EXAMPLE 17

4-Allyloxy-3-chloro-phenylacetyl-(DL)-phenylalanine methyl ester m.p. 69°–72.5° C.

Found: C,65.12; H,5.96; N,3.83; Cl,8.90. $C_{21}H_{22}NO_4Cl$ requires C,65.03; H,5.72; N,3.61; Cl,9.14%.

EXAMPLE 18

4-Allyloxy-3-chloro-phenylacetyl-(DL)-phenylalanine m.p. 110°–113° C.

Found: C,64.13; H,5.34; N,3.84; Cl,9.05. $C_{20}H_{20}NO_4Cl$ requires C,64.26; H,5.39; N,3.75; Cl,9.48%.

EXAMPLE 19

4-Allyloxy-3-chloro-phenylacetyl-(DL)-phenylalanyl-(DL)-phenylalanine methyl ester m.p. 120°–123° C.

Found: C,67.16; H,6.06; N,5.45; Cl,6.85. $C_{30}H_{31}N_2O_5Cl$ requires C,67.34; H,5.84; N,5.24; Cl,6.63%.

EXAMPLE 20

4-Allyloxy-3-chloro-phenylacetyl-(DL)-phenylalanyl-(DL)-phenylalanine m.p. 157°–160° C.

Found: C,66.45; H,5.82; N,5.52; Cl,6.72. $C_{29}H_{29}N_2O_5Cl$ requires C,66.85; H,5.61; N,5.38; Cl,6.80%.

EXAMPLE 21

4-Allyloxy-3-chloro-phenylacetyl-(DL)-phenylalanyl-(DL)-phenylalanyl-glycine methyl ester 4-Allyloxy-3-chloro-phenylacetyl-(DL)-phenylalanyl-(DL)-phenylalanine (1.20 g) was dissolved in dry tetrahydrofuran (10 ml). To the solution was added glycine methyl ester hydrochloride (0.25 g) in dry chloroform (10 ml) containing dry triethylamine (0.28 ml). DCC (0.41 g) was added and the reaction mixture was stirred overnight at room temperature. DCU was then filtered off.

The volatile material was evaporated at reduced pressure and the semi-solid residue was dissolved in chloroform (50 ml). The chloroform solution was washed with dilute hydrochloric acid (pH 2-3, 2×50 ml), saturated aqueous sodium bicarbonate (2×50 ml), and finally with water (2×50 ml). The extract was dried (anhydrous sodium sulphate) and concentrated to a small volume. Light petroleum (b.p. 80°-100° C.) was added to give a solid (100 mg) of m.p. 73°-80° C. After recrystallisation from chloroform/light petroleum (b.p. 40°-60° C.) the above-named product (80 mg), m.p. 77°-81° C., was obtained.

Found: C,64.58; H,5.76; N,7.29; Cl,5.85. $C_{32}H_{34}N_3O_6Cl$ requires C,64.91; H,5.79; N,7.10; Cl,5.98%.

EXAMPLE 22

4-n-Propoxy-3-chloro-phenylacetyl-glycine methyl ester

4-Allyloxy-3-chloro-phenylacetyl-glycine methyl ester (see Example 6; 3.0 g) was dissolved in absolute ethanol (100 ml) and Adams catalyst (20 mg) was added. Hydrogenation was carried out in an atmospheric pressure hydrogenator for 5 hrs. until hydrogen (310 ml) had been taken up. The catalyst was removed from the reaction mixture by filtration, the solvent was evaporated at reduced pressure, and light petroleum (b.p. 40°-60° C.) was added to the residue; a solid product (600 mg) of m.p. 76°-80° C. was obtained. After recrystallisation from chloroform/light petroleum (b.p. 40°-60° C.), the above-named product (200 mg), m.p. 79°-82° C., was obtained.

Found: C,55.86; H,5.91; N,4.61; Cl,11.88. $C_{14}H_{18}NO_4Cl$ requires C,56.09; H,6.05; N,4.67; Cl,11.83%.

EXAMPLE 23

4-n-Propoxy-3-chloro-phenylacetyl-glycine 4-n-Propoxy-3-chloro-phenylacetyl-glycine methyl ester was prepared as described in Example 22, but the oily residue obtained after the work-up procedure was not treated with light petroleum, but instead was suspended in acetone (80 ml) and aqueous sodium hydroxide (1M, 20.0 ml) was added to the suspension. The mixture was warmed at 40° C. for 30 min. to effect solution.

After cooling to 0° C., the pH was reduced to 2-3 using aqueous hydrochloric acid (3M), and the whole was extracted with ethyl acetate (100 ml). The extract was dried (anhydrous sodium sulphate) and the volatile material was evaporated at reduced pressure to give a small volume of material. Light petroleum (b.p. 40°-60° C.) was added to precipitate a solid (1.0 g) of m.p. 105°-110° C. After recrystallisation from ethyl acetate/light petroleum (b.p. 40°-60° C.), the above-named product (600 mg), m.p. 110°-112° C., was obtained.

Found: C,54.73; H,5.38; N,5.23; Cl,12.68. $C_{13}H_{16}NO_4Cl$ requires C,54.64; H,5.64; N,4.90; Cl,12.43%.

Certain compounds according to the invention have been subjected to pharmacological testing in order to assess their anti-inflammatory activity.

For this purpose, the well known test for the inhibition of experimentally-induced paw oedema in rats was used. The test was carried out as follows.

The rats are fasted 18 hours prior to dosing, but water is made available to them. Test compounds are then administered in aqueous 1% tragacanth at a dose volume of 25 ml/kg body weight. One group of rats is given vehicle only at the same dose volume. Forty five minutes later, all rats are given a subplantar injection of 0.1 ml of a 1% solution of carrageenin in 0.9% saline in the left hind paw. The volume of this paw is measured before and after the carrageenin injection using a volume differential meter designed by Ugo Basile.

Anti-inflammatory activity is measured as the percentage inhibition of paw oedema in the drug treated animals compared to the controls.

The compounds tested were as follows:
Compound 1 (as control): 4-allyloxy-3-chlorophenylacetic acid, Alclofenac
Compound 2: 4-allyloxy-3-chloro-phenylacetyl-(DL)-alanine methyl ester
Compound 3: 4-allyloxy-3-chloro-phenylacetyl-glycine
Compound 4: 4-n-propoxy-3-chloro-phenylacetyl-glycine The results obtained are shown in the following table:

| Test compound | Anti-inflammatory activity |
|---|---|
| 1 (control) | 36.0% |
| 2 | 23.1% |
| 3 | 34.6% |
| 4 | 35.2% |

What is claimed is:

1. A pharmaceutical composition comprising an anti-inflammatory effective amount of a peptide derivative of the formula:

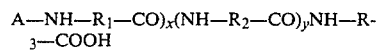

in which A is acetylsalicyloyl, 4-allyloxy-3-chlorophenylacetyl, or 4-n-propoxy-3-chloro-phenylacetyl;
$R_1$, $R_2$, and $R_3$ are the same or different and are each selected from the group consisting of residues of glycine, alanine, valine, leucine, isoleucine, serine, homoserine, threonine, proline, hydroxyproline, cysteine, homocysteine, methionine, phenylalanine, tyrosine, dopa, tryptophan, ornithine, lysine, hydroxylysine, histidine, aspartic acid, asparagine, glutamic acid, and glutamine;
x is 0 or 1;
y is 1 when A is acetylsalicyloyl, and 0 or 1 when A is 4-allyloxy-3-chloro-phenylacetyl or 4-n-propoxy-3-chlorophenylacetyl;
provided that x and y are not simultaneously zero;
or a physiologically acceptable salt or lower alkyl ester thereof, and an inert, physiologically acceptable carrier or excipient.

2. The composition according to claim 1, wherein $R_1$, $R_2$ and $R_3$ are residues of glycine, alanine, histidine or phenylalanine.

3. The composition according to claim 1, wherein:
A is 4-allyloxy-3-chloro-phenylacetyl or 4-n-propoxy-3-chloro-phenylacetyl,
x is 0,
y is 1, and
$R_2$ and $R_3$ are residues of glycine, alanine, or phenylalanine.

4. Peptide derivatives of the formula:

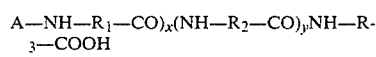

in which A is acetylsalicyloyl, 4-allyloxy-3-chloro-phenylacetyl, or 4-n-propoxy-3-chloro-phenylacetyl;

$R_1$, $R_2$, and $R_3$ are the same or different and are each selected from the group consisting of residues of glycine, alanine, valine, leucine, isoleucine, serine, homoserine, threonine, proline, hydroxyproline, cysteine, homocysteine, methionine, phenylalanine, tyrosine, dopa, tryptophan, ornithine, lysine, hydroxylysine, histidine, aspartic acid, asparagine, glutamic acid, and glutamine;

x is 0 or 1;

y is 1 when A is acetylsalicyloyl, and 0 or 1 when A is 4-allyloxy-3-chloro-phenylacetyl or 4-n-propoxy-3-chlorophenylacetyl;

provided that x and y are not simultaneously zero;

or a physiologically acceptable salt or lower alkyl ester thereof.

5. Derivatives according to claim 4, in which $R_1$, $R_2$ and $R_3$ are residues of glycine, alanine, histidine or phenylalanine.

6. Derivatives according to claim 4 in which:
A is 4-n-propoxy-3-chloro-phenylacetyl,
x is 0,
y is 1, and
$R_2$ and $R_3$ are residues derived from glycine, alanine or phenylalanine.

7. The compound according to claim 4 which is 4-allyloxy-3-chloro-phenylacetyl-L-phenylalanyl-L-phenylalanine methyl ester, and physiologically acceptable salts thereof.

8. The compound according to claim 4 which is 4-allyloxy-3-chlorophenyl-acetyl-L-phenylalanyl-L-phenylalanine, and physiologically acceptable salts thereof.

9. The compound according to claim 4 which is 4-allyloxy-3-chlorophenyl-acetyl-glycyl-glycine, and physiologically acceptable salts thereof.

* * * * *